US012631559B2

(12) United States Patent
Scholkmann et al.

(10) Patent No.: US 12,631,559 B2
(45) Date of Patent: May 19, 2026

(54) DEVICE AND METHOD FOR SPECTROSCOPIC MONITORING OF LIQUIDS

(71) Applicant: ARTHA AG, Schlieren (CH)

(72) Inventors: Felix Scholkmann, Zurich (CH); Peter Pfiffner, Herrliberg (CH)

(73) Assignee: Artha AG, Schlieren (CH)

( * ) Notice: Subject to any disclaimer, the term of this patent is extended or adjusted under 35 U.S.C. 154(b) by 407 days.

(21) Appl. No.: 18/556,121

(22) PCT Filed: Apr. 22, 2022

(86) PCT No.: PCT/EP2022/060704
§ 371 (c)(1),
(2) Date: Oct. 19, 2023

(87) PCT Pub. No.: WO2022/223788
PCT Pub. Date: Oct. 27, 2022

(65) Prior Publication Data
US 2024/0201087 A1 Jun. 20, 2024

(30) Foreign Application Priority Data

| Apr. 22, 2021 | (EP) | ..................................... | 21169925 |
| Apr. 22, 2021 | (EP) | ..................................... | 21169932 |

(51) Int. Cl.
*G01N 21/3577* (2014.01)
*G01N 21/64* (2006.01)
(Continued)

(52) U.S. Cl.
CPC ......... *G01N 21/6402* (2013.01); *G01N 21/65* (2013.01); *G01N 33/18* (2013.01)

(58) Field of Classification Search
CPC ........... G01N 21/6402; G01N 21/3577; G01N 21/65; G01N 33/18; G01N 21/33; G01N 33/1826; G01J 3/4406
See application file for complete search history.

(56) References Cited

U.S. PATENT DOCUMENTS

| 5,942,754 A | 8/1999 | Yamaguchi et al. |
| 7,812,946 B1 | 10/2010 | Killinger et al. |
| | (Continued) | |

FOREIGN PATENT DOCUMENTS

| CN | 110472819 A | 11/2019 |
| EP | 0985920 A1 | 3/2000 |
| | (Continued) | |

OTHER PUBLICATIONS

Rodriguez-Cuesta M.J. et al: "Determination of carbendazim, fuberidazole and thiabendazole by three-dimensional excitation-emission matrix fluorescence and parallel factor analysis", Analytica Chimica Acta, Elsevier, Amsterdam (NL), vol. 491, Sep. 1, 2003, pp. 47-56.
(Continued)

*Primary Examiner* — Abdullahi Nur
(74) *Attorney, Agent, or Firm* — Ipsilon USA—NLO

(57) ABSTRACT

The present disclosure relates to the field of spectroscopic monitoring of liquids. In particular, among other aspects, disclosed herein are novel Raman spectrometry (RS)- and laser-induced fluorescence (LIF)-enabled water quality monitoring devices, as well as methods, computer-implemented methods, or programmes for processing spectral
(Continued)

data received therefrom. The principles underlying the disclosed methods and products are suitable for analysis of any liquid, aqueous or non-aqueous, but are particularly well suited for analysis or monitoring of aqueous liquids, including industrial aqueous mixtures or suspensions, beverages, liquid dairy products, biological fluids, and notably water.

18 Claims, 3 Drawing Sheets

(51) Int. Cl.
  *G01N 21/65* (2006.01)
  *G01N 33/18* (2006.01)

(56) References Cited

U.S. PATENT DOCUMENTS

| | | | | |
|---|---|---|---|---|
| 8,848,173 | B2 * | 9/2014 | Poteet | G01N 21/47 |
| | | | | 356/73 |
| 10,101,209 | B2 * | 10/2018 | Selker | G01N 21/65 |
| 2005/0052645 | A1 | 3/2005 | Stewart et al. | |
| 2008/0245486 | A1 | 10/2008 | Brown | |
| 2012/0001094 | A1 | 1/2012 | Killinger et al. | |
| 2012/0316446 | A1 * | 12/2012 | Vukelic | G01N 21/65 |
| | | | | 600/476 |
| 2014/0211199 | A1 * | 7/2014 | Kuo | G01J 3/2803 |
| | | | | 356/73 |
| 2015/0377787 | A1 * | 12/2015 | Zeng | A61B 5/0071 |
| | | | | 356/301 |
| 2016/0091419 | A1 * | 3/2016 | Watson | G01N 33/02 |
| | | | | 356/407 |
| 2022/0044921 | A1 * | 2/2022 | McLoughlin | G01N 15/1459 |

FOREIGN PATENT DOCUMENTS

| | | | | |
|---|---|---|---|---|
| EP | 2856125 | B1 * | 7/2020 | G01N 23/223 |
| EP | 3164046 | B1 * | 10/2020 | G01J 3/44 |
| JP | S6212842 | A * | 1/1987 | |
| WO | WO-2014124531 | A1 * | 8/2014 | G01N 21/65 |

OTHER PUBLICATIONS

Hug, William F. et al: "Water & Surface contamination monitoring using deep UV laser induced native fluorescence and Raman spectroscopy", Proceedings of SPIE—The International Society for Optical Engineering—Oct. 2006.

Bartram, Jamie: "Water Quality Monitoring. A practical guide to the design and implementation of freshwater quality studies and monitoring programmes", London 1996.

Hasan, Jafrul: "Technologies and Techniques for Early Warning Systems to Monitor and Evaluate Drinking Water Quality: A State-of-the-Art Review", Office of Research and Development, National Homeland Security Research Center, Aug. 25, 2005.

Geladi, Paul: "Chemometrics in spectroscopy. Part 1. Classical chemometrics", Spectrochimica Acta Part B 58 (2003) 767-782.

Technical Program SPIE Optics East, Photonics for Applications in Industry, Life Sciences, and Communications Oct. 1-4, 2006.

* cited by examiner

DEVICE AND METHOD FOR SPECTROSCOPIC MONITORING OF LIQUIDS

TECHNICAL FIELD OF THE INVENTION

The present disclosure relates to the field of spectroscopic monitoring of liquids. In particular, among other aspects, disclosed herein are novel Raman spectrometry (RS)- and laser-induced fluorescence (LIF)-enabled liquid quality monitoring devices, as well as methods, computer-implemented methods, or programmes for processing spectral data received therefrom. The principles underlying the disclosed methods and products are suitable for analysis of any liquid, aqueous or non-aqueous, but are particularly well suited for analysis or monitoring of aqueous liquids, including industrial aqueous mixtures or suspensions, beverages, liquid dairy products, biological fluids, and notably water.

BACKGROUND OF THE INVENTION

The quick analysis of the components of liquid samples is crucial in modern day society. Not only the analysis of possible contaminants in a liquid sample is of relevance, also the determination of the concentration of the presence and concentration of a desired component in such a sample may be of relevance. This is particularly true for the medical industry, although a same need exists in other industries, such as the chemical industry, agriculture and food industry. A particularly relevant area wherein the (early) determination of contaminants is of particular relevance is in the production in drinking water.

Access to safe drinking water is a critical environmental as well as public health and security issue worldwide. Water is indispensable for our lives and for the sustainable development of our societies. The quality of freshwater resources however is under severe global pressure, primarily due to constant increase in human populations and activities causing, among others, industrial discharge of toxic chemicals, or high nitrate and pesticide contamination from agriculture [Bartram, J. and Balance, R; Water Quality Monitoring; ISBN 9780419223207].

However, given different territorial legislations, the already existing infrastructures and testing capacities, the reality is that many testing requirements of liquids, in particular aqueous liquids, are not unified. Consequently, in view of the rapidly growing urbanisation rate, industrial expansion, and a constant occurrence of new contaminants, rapid and sensitive devices for in-line industrial liquids monitoring are urgently needed, and thus avoid or mitigate the impacts of potential contamination events. In contrast however to the alternative approaches as proposed to date, such devices have to be designed to cooperate with the existing infrastructures like laboratories, as well as adapt to and build on the information provided therefrom in order to enhance the overall analytical speed and enable immediate local responses in case of hazardous substance detection events.

The quality of liquids, in particular aqueous liquids, can be characterized by concentrations of microbiological, organic and inorganic analytes, or by certain physical characteristics including pH, temperature or turbidity. Detailed review of currently available instruments and techniques for example in early detection of water quality indicators can be found in Hasan, J. et al., Technologies and Techniques for Early Warning Systems to Monitor and Evaluate Drinking Water Quality: A State-of-the-Art Review; EPA/600/R-05/156.

The document shows that many of the most reliable and sensitive analyses, like specific chemical or enzymatic reactions, chromatography including HPLC, or capillary electrophoresis etc., are still wet-laboratory based and require skilled personnel. The waiting times can be even longer in certain sectors of food and beverage industry, where some safety microbiological tests still rely on growth of the target microorganism in a specific medium or a dish, which can take days or even longer. Naturally, this negatively impacts on the costs and time of result delivery, which in turn causes delays in responses to potentially detrimental and hazardous contamination events. Similar problems are observed in other industries.

Furthermore, although high-speed spectroscopic-detection systems are presently used for in-line water or aqueous sample monitoring, the problem is that if these systems encounter a specific analyte or a contaminant, laboratory analysis have to be carried out to determine its identity. In other words, also these high-speed detection systems suffer from the relatively high costs and slow analysis by wet laboratories. Hence, a need remains for a quick and low-cost way of reliably samples and for the quick determination of contaminations found in various liquid products.

To address these needs of the different industries, hereby provided are spectroscopic monitoring devices and methods comprising a chemometric model and adapted to train it by performing chemometric analysis on sample spectral data vs chemical analysis data. By training the chemometric model, they achieve gradual elimination of the need to dispatch samples for wet-laboratory non-spectroscopic physico-chemical analyses. This is because the trained devices will eventually get acquainted with the frequently occurring analytes and eventually will only occasionally require the non-spectroscopically performed sample validations. Naturally, this is not only associated with reduced costs, but also with greatly enhanced response speeds in case of an undesired analyte's detection. Although the devices and methods presented herein were successfully tested on water samples, data indicates that they are generally applicable to liquid samples, in particular aqueous samples. Hence, in certain instances, the devices and methods are also expected to work on non-aqueous liquid samples, such as, organic solvents, oils or mixtures thereof. These and other features and advantages are explained further herein.

SUMMARY OF THE INVENTION

The present invention relates devices, computer-implemented methods, computer programmes and/or computer-readable media having stored thereon said programmes or results obtainable therefrom, as well as general methods and uses comprising or involving any of the above.

A first aspect of the invention relates to a method for monitoring a sample of a liquid according to claim 1. The method comprises the steps of iteratively performing:

analysing the sample by a combined laser-induced fluorescence (LIF) and Raman spectroscopy (RS) measurement thereby obtaining a first dataset representative for the spectral signature of the sample;

comparing the first dataset with a first reference spectrum dataset representative for the spectral signature of the liquid thereby obtaining a spectral deviation dataset;

associating the spectral deviation dataset with second reference spectra datasets representative for spectral signatures of one or more pollutants present in the liquid;

cancelling out the first dataset with the first reference spectrum dataset and second reference spectra datasets of associated pollutants thereby obtaining a spectral threshold dataset; and when one or more values of the spectral threshold dataset exceeds a predefined value;

triggering an event for indicating the one or more values as outliners.

In a first step, the liquid is analysed by a combined LIF-RS spectroscopy measurement, and more in particular a sample thereof. This way, a quick yet reliable measurement can be performed having a high sensitivity because of the LIF spectroscopy measurement and a high level of specificity at a reduced sensitivity by the RS spectroscopy measurement. This measurement results in a first dataset, further denominated as the dataset, which represents the spectral signature of the liquid that is monitored.

Additionally, to the LIF-RS spectroscopy measurement, the method may also measure other parameters, like a pH value, a temperature, a turbidity, and/or a conductivity of the liquid, or a sample thereof. The first dataset, and the other used dataset, like the first reference spectrum dataset, and the second reference spectra datasets are then normalized dataset based on this parameter. The next steps may then be performed by taking into account the parameter, thereby increasing the accuracy of the monitoring of the liquid.

The spectral signature of the liquid presented by the dataset is representative for the physical and chemical properties of the liquid.

The dataset may comprise a matrix representing the spectral signature, and/or any other suitable data representation and adapted for further processing.

In a second step, the dataset representing the spectral signature of the liquid is compared with a reference spectrum dataset of the liquid, and in particular with a dataset representing the spectral signature of the liquid and in a same format as the dataset resulting from the LIF-RS spectroscopy measurement.

The dataset representing the spectral signature of the liquid is, for example, initially obtained by performing a LIF-RS spectroscopy measurement on the liquid in its pure, or nearly pure, form. Alternatively, or additionally, the dataset may also be obtained by performing other measurements which also result in the spectral signature of the liquid in its pure, nor nearly pure, form.

By comparing the spectral signature of the liquid in its pure or nearly pure form with the dataset obtained by the combined LIF-RS spectroscopy measurement, a spectral deviation dataset is obtained. This dataset represents the deviation between the liquid in its pure or nearly pure form, and the liquid comprising one or more pollutants, i.e. the liquid not in its pure form. Therefore, the spectral deviation dataset is representative for pollutants present in the liquid.

Next, in a third step, the spectral deviation dataset is associated with second reference spectra datasets which one their turn represents the spectral signatures of pollutants which may be present and/or are present in the liquid. In other words, by associating the spectral deviation dataset with the second reference datasets, one or more pollutants present in the liquid are be identified. In an embodiment, these associated and therefore identified pollutants may be reported to a user as an additional step of the computer-implemented method.

Additionally and in a preferred embodiment, the second reference datasets are also representative for the presence of one or more pollutants in the liquid together with a respective concentration thereof. This further implies that for a same pollutant more than one dataset may be used, wherein each data set is representative for the presence of the pollutant each with a different concentration.

In a fourth step, the dataset obtained by the combined LIF-RS spectroscopy measurement is cancelled out or filtered by the reference spectrum of the liquid and the reference spectra of the associated or identified pollutants. As a result, a spectral threshold dataset is obtained.

The spectral threshold dataset is therefore indicative for one or more pollutants present in the liquid, but that were not identified by the associating step.

Next, the spectral threshold dataset is inspected and if one or more values of the spectral threshold dataset exceeds a predefined value, the computer-implemented method triggers an event. This event indicates that there are one or more outliners present in the spectral threshold dataset.

The event may, for example, be an alarm, a sound, the sending and/or projecting of a report, an email, a text message, a light, a screenshot, and/or any other suitable event that may be triggered for informing a user that one or more outliners are detected.

Advantageously, instead of comparing datasets obtained from measurements one on one with datasets stored on a database, the method first compares the dataset with one which represents the liquid in its pure form, or nearly pure form. This way, firstly, an indication is given how pure or clear the monitored liquid is. Secondly, through the obtained spectral deviation dataset, pollutants present in the liquid are identified, optionally and preferably with their respective concentration. This way, a user may be notified of the presence of the pollutants, in case with the concentration, and may based thereon undertake adequate interventions if needed.

Next, by cancelling out the dataset obtained by the LIF-RS spectroscopy measurement with the reference spectrum dataset of the liquid and the associated pollutants, in case with the corresponding concentration, a dataset is obtained which is representative for spectral signatures of pollutants present or that may be present in the liquid but not yet identified.

Furthermore, this way, a user will only be triggered to further investigate the liquid, or a sample thereof, when there are unidentified pollutants, and/or unidentified concentrations thereof, present in the liquid.

According to an embodiment, the second reference spectra datasets may be updated based on data received from an analysis step of identifying the outliners as one or more additional pollutants.

In other words, after a user is notified that unidentified pollutants, and/or unidentified concentrations thereof, are present in the liquid, the user may perform an in-depth analysis of the liquid using other methods than the LIF-RS spectroscopy measurement. After the in-depth analysis is performed, the computer-implemented method may update the data it uses.

This way, on the one hand, the method is suitable for performing a fast and efficient monitoring of the liquid by the combined use of LIF-RS spectroscopy, and on the other hand will only trigger a user to perform further in-depth analysis based on an objective yet reliable event. Therefore, it is avoided that a user will perform said in-depth analysis of a liquid when this would be redundant.

Next, after performing an in-depth analysis of the liquid, the second reference spectra datasets are updated based on the data received from said in-depth analysis step. The outliners previously identified as outliners will therefore no longer be identified as outliners, but associated as one or more pollutants, in case with their respective concentrations. Thus, by updating the reference spectra datasets after performing the in-depth analysis, the accuracy of method itself increases through a self-learning process caused by this updating step.

Additionally, according to an embodiment, a health status of the liquid may be reported based on the spectral threshold dataset and/or the event. In other words, besides reporting the associated one or more pollutants, the method may also indicate the status as being, for example, acceptable, non-acceptable, critical, non-critical, or any other term which indicates the health status of the liquid.

Alternatively, the health status may also be reported using a colour, like green for a good health status, red for a bad one, and orange for a critical health status.

In a second aspect, the invention relates to a system for spectroscopic analysis of a liquid according to claim 9. The system comprises:

- monitoring means for monitoring the liquid in a conduit and/or a container via a deep ultraviolet (UV) spectroscopy arrangement comprising a laser for irradiating the liquid, the arrangement being adapted to perform laser-induced fluorescence (LIF) and Raman spectroscopy (RS) measurements; and
- a processing unit configured to receive data from the UV spectroscopy arrangement and to perform the method according to the first aspect based on the received data.

In a third aspect, the invention relates to a device for spectroscopic analysis of a liquid according to claim 10. The device comprises:

- a conduit and/or a container;
- a deep ultraviolet (UV) spectroscopy arrangement comprising a laser for irradiating the liquid, the arrangement being adapted to perform laser-induced fluorescence (LIF) and Raman spectroscopy (RS) measurements of the liquid in the conduit and/or container; and
- a processing unit configured to receive data from the UV spectroscopy arrangement and to perform the method according to the first aspect based on the received data.

As used herein, the term "conduit" refers to any structure in which a fluid such as liquid may flow from a first location to a second location and may be of any size or shape. Then, the term "container" as used broadly refers to any solid (e.g. flexible or rigid) structure that is capable of containing (holding) a liquid. Possible conduits or containers may have one or more sidewalls, and in case of being disclosed as substantially cylindrical, they can be regarded as having a single circumferential sidewall that forms a he shape of a cylinder. Possibly, for the ease of performing optical measurement, some conduits or containers may comprise a wall or a part thereof that is substantially transparent to the light as used in the optical measurement.

According to an embodiment, the device further comprises displaying means for presenting information indicative for the associated one or more pollutants and/or the event. The information can then be presented as text, graphs, numbers, or a combination thereof.

According to an embodiment, the device may further comprise a mechanical arrangement configured to collect a volume of the liquid, wherein the mechanical arrangement is activatable based on the associated one or more pollutants and/or the event. Preferably, the mechanical arrangement is detachable. This way, when outliners are detected, an in-depth analysis of a sample of the liquid can be performed in an efficient manner as further discussed in in the detailed description of the invention.

According to an embodiment, the conduit and/or container are configured to be connectable to a supply source of the liquid. Additionally, it may comprise blocking means configured to block the supply source based on associated one or more pollutants and/or the event. This way, when outliners are detected, the supply source may be blocked automatically.

In a fourth aspect, the invention relates to a computer program product comprising instructions to cause the device of the third aspect to execute the steps of the method of the first aspect.

In a fifth aspect, the invention relates to a computer-readable medium having stored thereon the computer program of the fourth aspect.

In a sixth aspect, the invention relates to a database comprising means for interacting with a data processing apparatus system comprising means for carrying out the method of the first aspect, the database stored thereon a first dataset with a first reference spectrum dataset representative for the spectral signature of a liquid, and second reference spectra datasets representative for the spectral signatures of one or more pollutants present in the liquid.

A further aspect of the present invention relates to a device comprising an activatable mechanical and/or fluidic arrangement configured to collect a volume of the test liquid sample.

Another aspect of the present invention relates to a computer-implemented method for spectroscopic analysis of a liquid, preferably being an aqueous liquid, the method comprising:

- receiving a chemometric model defining custom analytes
- receiving data from a deep ultraviolet (UV) spectroscopy system adapted to perform laser-induced fluorescence (LIF) and Raman spectroscopy (RS) measurements on a liquid sample, wherein said data comprises:
  - reference spectral data obtained from a LIF-RS measurement performed on a reference liquid sample, or predefined LIF-RS reference spectral data for a given liquid type; and
  - first test sample spectral data obtained from a LIF-RS measurement performed on a first test liquid sample; and
  - second test sample spectral data obtained from a LIF-RS measurement performed on a second test liquid sample;
- receiving a first test sample chemical parameters data obtained from a wet-laboratory non-spectroscopic analysis of a volume of the first test liquid sample;
- carrying out chemometric analysis on the first test sample spectral data versus the first test sample chemical parameters data, and updating the chemometric model;
- receiving spectral threshold data;
- computing the predefined LIF-RS reference spectral data or the reference spectral data and second test sample spectral data to quantify second test sample wavelength-dependent deviations
- processing of the second test sample wavelength-dependent deviations, said processing comprising
  - assessment of the second test sample wavelength-dependent deviations versus the spectral threshold data to determine whether an analyte is detected in the second test sample, and association of the second test sample wavelength-dependent deviations versus the updated chemometric model, if possible; and reporting to the user if an analyte is detected in the second test sample and, if the association was possible, identifying the detected analyte.

A further aspect of the present invention relates to a computer-readable medium having stored thereon the updated chemometric model as obtainable by operation of the device of the present invention or by performing of the computer-implemented method as also disclosed herein.

A last aspect of the present invention relates to uses of the devices, computer-implemented methods, software, and/or the computer readable media according to the present invention for analysis or monitoring of a liquid, preferably in chemical industry, automotive and aircraft industry, in steel and power generation, in glass manufacture and coating, in paint production, semiconductor industry, pharmaceutical industry, preferably drug production, phytopharmaceutical industry, in diagnostics, in agriculture, in biotechnology, in wastewater industry, in drinking water industry, in cosmetics production, in food production such as in dairy production or sugar mills, or in beverage production such as in brewing, as well as in production of oils and fuels.

BRIEF DESCRIPTION OF FIGURES

For a complete understanding of the nature of present disclosure, reference is made to the following detailed description taken in conjunction with the accompanying FIG. 1, which shows a schematic concept of a possible embodiment of a process as implemented by the herein disclosed self-learning water quality analytical device based on deep UV laser-induced fluorescence (LIF) and Raman spectroscopy (RS) combined with analytical chemical analysis. Legend of FIG. 1: $S(\lambda)$: measured UV LIF-RS spectra; $SRefl(\lambda)$: static reference spectrum; AUC: area under the curve; $\alpha$: wavelength-dependent scaling factor; T: threshold value; N: threshold value; $\beta$: parameter-dependent scaling factor; $q(p)$: quantity of parameter (p).

DETAILED DESCRIPTION OF THE INVENTION

Figure 1:
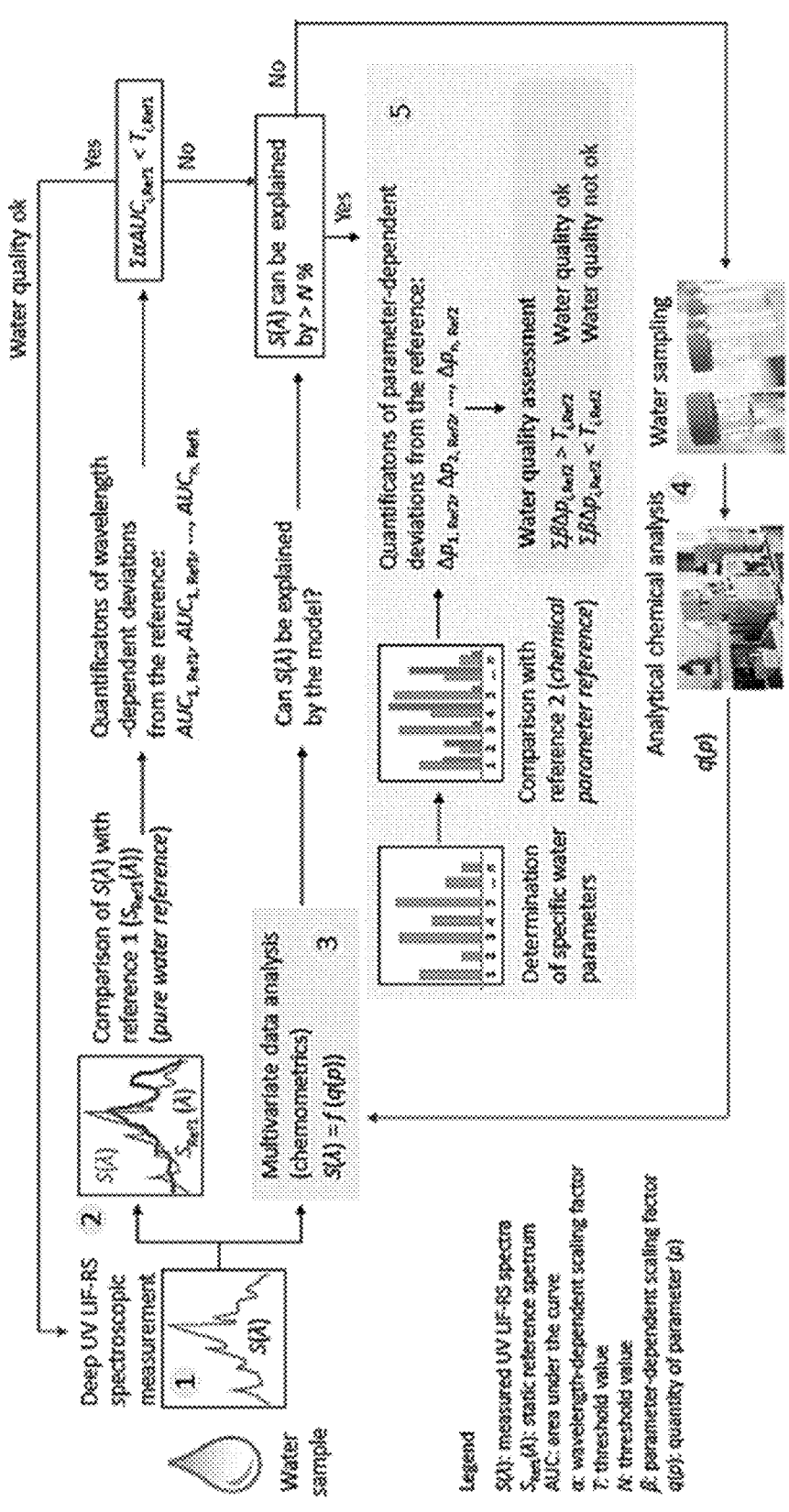

To address the urgent need for highly-adaptable, versatile, rapid, and sensitive in-line liquid monitoring, the present invention provides a combined approach of LIF-RS spectroscopy and iterative chemometrics-based detection devices, computer-implemented methods, computer programmes and/or computer-readable media having stored thereon said programmes or results obtainable therefrom, as well as general methods and uses comprising or involving any of the above. The presented herein approaches are applicable to monitoring of a wide variety of liquids, and are particularly suitable for aqueous liquids and water.

It is to be understood that other embodiments may be utilised and structural or logical changes may be made without departing from the scope of the present invention. The following detailed description, therefore, is not to be taken in a limiting sense, and the scope of the present invention is defined by the appended claims. The embodiments described herein use specific language, which should not be construed as limiting the scope of the appended claims.

A first aspect of the present invention relates to a device for spectroscopic analysis of a liquid, the device comprising:

a conduit or a container for monitoring a liquid sample;

a deep ultraviolet (UV) spectroscopy system comprising a laser for irradiating the liquid sample inside the conduit or the container, the system being adapted to perform laser-induced fluorescence (LIF) and Raman spectroscopy (RS) measurements, further referred to as LIF-RS measurements; and a computer comprising software for chemometric analysis;

wherein the device is configured to:

receive spectral threshold data and a chemometric model defining custom analytes;

receive chemical parameters data obtained from a liquid sample analysed by a wet-laboratory non-spectroscopic technique;

initiate the chemometric analysis and update the chemometric model when the chemical parameters data is received;

receive predefined LIF-RS reference spectral data or perform a LIF-RS measurement on a reference liquid sample to obtain reference spectral data, and perform a LIF-RS measurement on a test liquid sample to obtain test sample spectral data, then compute the predefined LIF-RS reference spectral data or the reference spectral data and test sample spectral data to quantify wavelength-dependent deviations;

process the wavelength-dependent deviations, wherein the processing comprises:

assessment of the wavelength-dependent deviations versus the spectral threshold data to determine whether an analyte is detected, and association of the wavelength-dependent deviations versus the chemometric model, if possible; and report if an analyte is detected and, if the association was possible, identify the detected analyte.

In an embodiment, the liquid sample is an aqueous liquid. In another embodiment, the liquid sample is water, whether or not polluted.

A specific aspect of the present invention relates to a device for spectroscopic analysis of an aqueous liquid, the device comprising:

a conduit or a container for monitoring an aqueous sample;

a deep ultraviolet (UV) spectroscopy system comprising a laser for irradiating the aqueous sample inside the conduit or the container, the system being adapted to perform laser-induced fluorescence (LIF) and Raman spectroscopy (RS) measurements, further referred to as LIF-RS measurements; and a computer comprising software for chemometric analysis;

wherein the device is configured to:

receive spectral threshold data and a chemometric model defining custom analytes;

receive chemical parameters data obtained from an aqueous sample analysed by a wet-laboratory non-spectroscopic technique;

initiate the chemometric analysis and update the chemometric model when the chemical parameters data is received;

receive predefined LIF-RS reference spectral data or
   perform a LIF-RS measurement on a reference aqueous
   sample to obtain reference spectral data, and
perform a LIF-RS measurement on a test aqueous sample
   to obtain test sample spectral data, then compute the
   predefined LIF-RS reference spectral data or the refer-
   ence spectral data and test sample spectral data to
   quantify wavelength-dependent deviations;
process the wavelength-dependent deviations, wherein
   the processing comprises:
   assessment of the wavelength-dependent deviations
      versus the spectral threshold data to determine
      whether an analyte is detected, and
   association of the wavelength-dependent deviations
      versus the chemometric model, if possible; and
   report if an analyte is detected and, if the association was
      possible, identify the detected analyte.
In a further embodiment, the aqueous liquid is selected
from a liquid diary product, preferably being milk, modified
milk or milk derivative, cream, yoghurt, or kefir; a beverage,
preferably being juice like a fruit or vegetable juice, wine,
vinegar, beer; or a biological sample, preferably being a
bodily fluid, most preferably being selected blood plasma,
blood serum, lymph, urine, cerebrospinal fluid, tears, spu-
tum, or amniotic fluid, or wherein the aqueous sample is
water.
   A more specific aspect of the present invention relates to
a device for spectroscopic analysis of water, the device
comprising:
   a conduit or a container for monitoring a water sample;
   a deep ultraviolet (UV) spectroscopy system comprising
      a laser for irradiating the water sample inside the
      conduit or the container, the system being adapted to
      perform laser-induced fluorescence (LIF) and Raman
      spectroscopy (RS) measurements, further referred to as
      LIF-RS measurements; and
   a computer comprising software for chemometric analy-
      sis; wherein the device is configured to:
   receive spectral threshold data and a chemometric model
      defining custom water pollutants;
   receive chemical parameters data obtained from a water
      sample analysed by a wet-laboratory non-spectroscopic
      technique;
   initiate the chemometric analysis and update the chemo-
      metric model when the chemical parameters data is
      received;
   perform a LIF-RS measurement on a pure water sample to
      obtain pure water reference spectral data, and on a test
      water sample to obtain test sample spectral data, then
      compute the pure water reference spectral data and test
      sample spectral data to quantify wavelength-dependent
      deviations;
   process the wavelength-dependent deviations, wherein
      the processing comprises:
      assessment of the wavelength-dependent deviations
         versus the spectral threshold data to determine
         whether a water pollutant is detected, and
      association of the wavelength-dependent deviations
         versus the chemometric model, if possible; and
   report, e.g. to the user, if a water pollutant is detected and,
      if the association was possible, identify the detected
      water pollutant.
   For a better understanding of the above and related
aspects of present invention, the following embodiments and
further definitions of the terms used to describe the present
invention are provided below. In this regard it is noted that
unless specifically mentioned otherwise, all terms as used herein have the same meaning as they would to a skilled
practitioner having general knowledge of the field. Conse-
quently, the terms and/or definitions provided herein should
not be construed to have a scope narrower than would be
understood by a person of ordinary skill in the art.
   As used herein, the singular forms "a", "an", and "the"
include both singular and plural referents unless the context
clearly dictates otherwise.
   The terms "comprise", "include", or "contain" as used
herein are synonymous and are inclusive or open-ended and
do not exclude presence of additional, non-recited features,
members, elements or method steps.
   The term "analyte" is intended to mean any chemical,
biochemical or biological entity which is desired to be
analysed, that is to say detected or identified, and/or possibly
quantitatively analysed and/or measured. An analyte can be
an undesired substance, termed "pollutant" or a "contami-
nant", such as water pollutant, but it can be any other
chemical or biological substance such as a drug, a metabo-
lised drug, peptide, protein, lipid, nucleic acid, a virus,
bacteria, eukaryotic pathogen, or a marker or hormone
regardless of their chemical nature etc.
   The term "liquid" refers to a fluid in substantially liquid
phase that has the property of conforming to the shape of its
container. Liquids are frequently referred to as having a
(nearly) definite volume but no fixed shape. Unlike a gas, a
liquid does not disperse to fill every space of a container, and
maintains a fairly constant density, though for some liquids
the latter can be influenced by pressure. A distinctive prop-
erty of the liquid is surface tension, leading to wetting
phenomena. The term liquid includes the term non-aqueous
liquid as well as the term aqueous liquid that includes the
term water, which is by far the most common liquid on
Earth. Other substances that are liquid under normal tem-
perature and pressure (NTP) conditions include many
organic solvents, like low molecular alcohols notably
including ethanol, butanol, isopropanol etc., as well as
numerous mixtures of different substances such as organic
or mineral oils, gasoline, aqueous emulsions like vinaigrette
or mayonnaise, suspensions like blood, and colloids like
paint and milk.
   The term "non-aqueous liquid" as used herein refers to
any liquid comprising anywhere between less than about
10% by weight of molecular water to the condition of having
no detectable molecular water.
   The term "aqueous liquid" refers to a liquid which is
either water or a liquid that contains water and is not a
non-aqueous liquid as defined above. Notable examples of
aqueous liquids include biological liquids, frequently termed
"biological fluids" or "biofluids", being aqueous liquids
from living organisms such as plants or animals including
humans. Biofluids from animals or humans are frequently
termed body fluids or bodily fluids. Biological fluids include
but are not limited to blood, plasma, serum, urine, cerebro-
spinal fluid, synovial fluid, pleural fluid (pleural lavage),
pericardial fluid, peritoneal fluid, amniotic fluid, saliva,
nasal fluid, otic fluid, gastric fluid, breast milk, as well as cell
culture supernatants. Other aqueous liquids include various
agricultural products or intermediate stages thereof, as well
as food and beverage products or intermediate stages
thereof, including juices, carbonated beverages, wine, vin-
egar, must, beer, must, baby food and drinks, liquid dairy
products such as milk, whole milk, different levels of
skimmed milk, or modified forms of milk, cream, yoghurt
etc.
   As used herein the term "water" shall refer to any volume
of water collected from a water source and shall not be limited to "molecular water" i.e. being 100% pure liquid form of a chemical substance given by chemical formula $H_2O$. The water source includes, but is not limited to, surface water (lakes, rivers, reservoirs, oceans, etc.), groundwater, wastewater (i.e., sewage), recreational water (water used for the purpose of recreation, i.e., swimming pool, spa, water-parks, etc.), and finished water (delivered to a distribution system after treatment, if any). Water can be either treated or untreated. Treated water has undergone a disinfection process (e.g., chlorination, filtration) for the purpose of making it safe.

As used herein, the term "pure water" shall mean water that is filtered or otherwise processed to remove soluble and/or insoluble impurities such as, but not limited to minerals, salts, suspended particles, bacteria, and others. Pure water shall include water processed by methods such as, but not limited to, distilling (i.e., distilled water), deionizing (DI water), also known demineralizing (DM), reverse osmosis, desalination, carbon filtration, microfiltration, ultrafiltration, ultraviolet oxidation, electrodialysis, others, and any combinations thereof.

As used herein, the term "sample" shall refer to the object of an analysis technique. The term "liquid sample" is intended to mean any sample comprising or substantially made of a dissolving or dispersing medium an in liquid state, in which medium the analyte in question is in solution or suspension. The dispersing medium can be non-aqueous or aqueous, depending whether it is substantially made of a non-aqueous liquid or an aqueous liquid.

In present particular context, a "water sample" is to be construed as a sub volume of a volume of water, which can be an object of several analysis techniques for as long as smaller sub volumes can be obtained therefrom a subjected to said analysis techniques e.g. in parallel or sequentially.

The term "spectroscopy" refers generally to a process of measuring energy or intensity as a function of wavelength in a beam of light or radiation. Specifically, spectroscopy studies physical properties of a material using absorption, emission, and/or scattering of electromagnetic radiation by atoms, molecules, and/or ions within the material. In line with this, the term "spectroscopy system" is to be construed as any arrangement of elements allowing to perform spectroscopic measurements, which can be described as measurement set-ups. Such measurement set-up would normally comprise at least a source of light or radiation (also referred to as the "radiation source" or "excitation source", which, as used herein should be construed as synonyms), and at least a spectroscopic sensor or detector.

Further, as the term "deep ultraviolet" or "deep UV" as used herein is to be construed as relating to radiation with a wavelength between 190 nm to 270 nm, the terms "deep ultraviolet spectroscopy system" or "deep UV spectroscopy system" are to be construed as describing a spectroscopy system comprising a source of light or radiation, configured to emit radiation with a wavelength between 190 nm to 270 nm. Advantageous deep UV wavelength lies between 220 nm and 250 nm, and even more advantageously the wavelength is at least 230 nm and/or at most 240 nm. The radiation emitted by the excitation source may be substantially narrow in its wavelength range, i.e. the full width at half maximum (FWHM) may be substantially less than 1 nm. The excitation source will likely be a laser, preferably selected from the group consisting of a microchip laser unit, a solid-state laser, a gas laser, or a hollow cathode ion laser. Further suitable examples of excitation source can be found in a U.S. patent application Ser. No. 11/245,486 or in Hug, W. F. et al., 2006, Proceedings of SPIE, vol, 6378.

The term "Raman spectroscopy" or "RS" as used herein, refers generally to spectroscopy that relies on an inelastic scattering of, usually, intense monochromatic light from an excitation source, such as a laser that operates in any of ultraviolet, visible, or infrared light range. Photons of the monochromatic light source excite molecules in the material upon inelastic interaction, which results in the energy of the scattered laser photons being shifted down to a lower frequency (lower energy level, so called Stokes shift) or up to a higher frequency level (anti-Stokes shift). This energy shift yields information about molecular vibration modes of the material being studied. Deep UV Raman spectroscopy is a mode of RS employing measurements carried out in the deep UV range, as defined above. Notably, deep UV Raman spectroscopy can result in signal intensities orders of magnitude higher than signal intensities observed in "classic" Raman measurements employing excitation sources with wavelengths in the visible to near-infrared ranges. Optionally, the wavelength of the excitation source can be adapted to perform resonant Raman spectroscopy, which may result in even more considerable signal intensities.

One of the drawbacks of carrying out Raman measurements at wavelengths shorter than the commonly employed visible to near-infrared wavelength range may be the occurrence of fluorescence radiation, wherein fluorescence signal intensities can be substantially greater than Raman signal intensities. However, empirically it was found that fluorescence signal intensities are very moderate or even negligible for most components when excitation sources with a wavelength in the deep UV are employed, preferably with wavelengths no larger than 250 nm and most preferably with wavelengths no larger than 240 nm.

Further, the term "laser-induced fluorescence spectroscopy" or "LIF" as used herein, refers to a spectroscopic method where sample atoms or molecules are excited to a higher energy level by the absorption of pulsed or continuous laser light followed by spontaneous emission of light, which produces time and wavelength resolved fluorescence spectra of the sample. For completeness, the term "deep UV LIF spectroscopy" refers to a mode of LIF spectroscopy employing as the radiation source a laser configured to emit radiation with a wavelength between 190 nm to 270 nm.

In an embodiment of the present invention the system may comprise at least one deep UV radiation emitting laser as the radiation source, a first measurement set-up for performing deep UV Raman measurements and comprising a first detector being a spectrometer, like a Michelson spectrometer or a Fourier-transform spectrometer, and a second measurement set-up for measuring LIF emitted by the a sample as a result of absorption of the laser radiation. The second measurement set-up may be suitable for detecting radiation with a wavelength between 260 nm and 600 nm, possibly at multiple time-delayed instances, thereby enabling insight with respect to the fluorescence lifetime of at least some of the components in the test sample. The second measurement set-up may comprise a second detector that may also be any spectrometer, like a Michelson or a Fourier-transform spectrometer. In a possible integrated embodiment, the first detector may also detect the radiation with a wavelength between 260 nm and 600 nm and the deep UV spectroscopy system can be configured for carrying out both the measurements in the first measurement set-up and second measurement set-up with the same excitation source and with the first detector, which may result in substantially reducing the time to conclude the quantitative and qualitative analysis of a test sample, as opposed to a hypothetical modular system comprising analysing the test sample in a first deep UV Raman system and then subsequently in a second LIF system.

In further embodiments of the present invention, the deep UV spectroscopy system or the device of the disclosure comprising the latter, may further comprise a third (or more) measurement set-up, the third measurement set-up being configured for performing a further spectroscopic analysis technique like e.g. selected from the group consisting of UV-visible absorption spectroscopy, infrared (IR) absorption spectroscopy, IR emission spectroscopy, laser-induced breakdown spectroscopy (LIBS), or magnetic resonance spectroscopy technology like magnetic resonance imaging based measurement of relaxation times etc. In an advantageous embodiment, the deep UV spectroscopy system may further comprise a near-infrared (NIR) spectrometer and be adapted to further perform near-infrared spectrometry (or NIRS), i.e. spectrometry that uses the electromagnetic spectrum comprised within the region from 650 nm to 2500 nm.

Then, as used herein the term "computer" refers to hardware that generally implements functionality provided by digital computing technology, particularly computing functionality associated with microprocessors. In particular embodiments, the term may refer to a single device but in other embodiments, it may include several devices; for example, functionally it may comprise, reside on, or be spread between multiple servers. Thus, as used herein, the term "computer" is not intended to be limited to any specific type of a computing device, but it is intended to be inclusive of all computational devices notably including processing devices or microprocessors (possibly referred to in simplification as processor, processing units, or even CPUs). The term may refer to a single processor or a group of singular processors, but it may also refer to personal computers, desktop computers, laptop computers, workstations, terminals, servers, clients, portable computers, handheld computers, smart phones, tablet computers, mobile devices, and wearable computing devices including but not limited to wristwear like watches or eyewear like glasses. The computer will usually comprise a so called "computer-readable storage medium", also referred to as a "machine-readable medium", or several of such "computer readable media", usually being a magnetic disc or a card. Typically, computer-readable media can receive or store data or instructions of e.g. how the computers operates and/or communicates with other linked or connected thereto hardware such as a screen or the deep UV spectroscopy system. The computer-readable media can store data received from the user or from the system, as well as such data as further processed by the computer, or any other software, like an operating system, specific computer programme, application, script, and the like.

In the context of the present disclosure, the term "computer" can be construed as comprising a signal processing unit that comprises a pre-processing unit configured to receive data provided from any data collecting device, like a spectroscope or a spectroscopy system, connected to the computer.

For example, when conducting a measurement by an embodiment of a deep UV spectroscopy system, a first measurement set-up generates a data array $R(\lambda,I)$ and a second measurement set-up generates a new data array $A(\lambda,I)$. Then, the pre-processing unit receives the data generated by the first measurement set-up and by the second measurement set-up, after which the received data are processed by the signal processing unit. The pre-processing unit may receive data via an interconnection between each of the first and second measurement set-ups (as well as the third or further measurement set-ups, if present) and the pre-processing unit and may be based on a Wi-Fi connection, a Bluetooth connection, a physical wire or on a printed circuit board. Consequently, as used herein, the term "computer" is to be construed as an abstraction of the functionality provided by computing devices outfitted with additional hardware and accessories typical thereof rather than any concrete physical entity.

As used herein the terms "spectral data" or "spectroscopic data" can be used interchangeably and may encompass both the raw or mathematically processed or transformed numerical data obtained by the spectroscopic measurement, for example a LIF-RS measurement.

In the particular context of the present disclosure, the term "pure water reference spectral data" refers to data obtained from a LIF-RS measurement performed on a pure water sample. The pure water reference spectral data comprises spectral information associated with pure water, such as Raman water peak; which can be used for system calibration and/or for calibration of the measurements performed on water to be tested ("test water") or an aqueous sample ("test aqueous sample)".

As used herein, the term "reference spectral data" refers to data obtained from a LIF-RS measurement performed on a liquid or aqueous sample that is used as a reference (i.e. reference liquid sample or reference aqueous sample, respectively) e.g. for calibration purposes. A typical reference sample can be a substantially pure dissolving or dispersing medium, in which the analyte in question is in solution or suspension. For example, for analysing a mixture of chemicals dissolved in any one of ethanol, acetone, isooctane, methanol, hexane, or any specific mixture thereof, the reference sample will be either of ethanol, acetone, isooctane, methanol, hexane, or the specific mixture thereof, respectively. Most typical reference sample for water and aqueous mixtures will be pure water sample. Alternatively, a reference sample for, e.g. more complex samples, can be a sample of the same type but verified or well characterised by the contained thereby analytes. For biological samples, frequently such well characterised reference sample may not be available, so alternatively, a predefined LIF-RS reference spectral data may be used. For example, for analysing plasma from a cancer patient for presence of cancer markers, comparison with the same patient's healthy plasma will not be possible, so a predefined LIF-RS reference spectral data obtained by averaging spectral data from very many healthy e.g. age- and/or gender-matched individuals could be used instead.

The term "test sample spectral data" refers to data obtained from a LIF-RS measurement performed on a liquid or aqueous or water sample ("test sample") that is the object of the analysis.

Further, the term "calibrated test sample spectral data" is to be construed as test sample spectral data that was calibrated based on predefined LIF-RS reference spectral data, reference spectral data, or pure water reference spectral data. In case of the latter, the calibrating can be done for example by scaling the test sample spectral data against the spectral information associated with pure water, for example the Raman water peak.

As used herein the term "wavelength-dependent deviations" refers to quantified deviations between the pure water reference spectral data and the test sample spectral data.

As used therein the term "custom pollutant" or "custom contaminant" is to be interpreted as referring to any chemical or biochemical substance or biological microorganism that can be considered or custom defined as undesired in the liquids of interest.

In further aspect the devices or computer-implemented methods according to the present invention are in fact "software for chemometric analysis", which term can be construed as computer-readable or executable instructions for performing chemometric analysis.

As used herein, the term "chemometric analysis" is to be construed as multivariate calibration in combination with data pre-processing and classification, resulting in the construction of a chemometric model that links spectroscopic data obtained from a spectroscopic analysis of a sample ("sample spectral data") with non-spectroscopic data ("chemical parameters data") obtained from a non-spectroscopic chemical analysis (as use herein "wet-laboratory non-spectroscopic analysis") of the sample.

As used herein the term "chemometric model" is to be construed as a mathematical function comprising an equation combined with a matrix of numerical data, which is linking the spectroscopic data to the non-spectroscopic chemical data.

In the context of the present disclosure, the chemometric model can be interpreted as defining at least a characteristic or a set of characteristics for a number of custom pollutants, wherein said a least one characteristic at least allows to link a name of or a label describing a custom pollutant to its spectral fingerprint that the devices or methods according to the present invention will identify or learn to identify.

The characteristics can be qualitative (e.g. identification of a name) or quantitative (e.g. relative amount or concentration or an estimation thereof). In addition to characteristics defining custom pollutants, the chemometric model may further define characteristics of other physico-chemical parameters or properties of the liquid of interest. In an embodiment of the present invention, such parameters may include desired water qualities such as minerals etc.

Mathematical determination of a chemometric model is part of the chemometric analysis, so in principle no extra methods or algorithms are needed to update or modify the chemometric model once new data is received for performing the chemometric analysis.

In general, the term "chemometric" as used herein refers to the use of statistical and mathematical techniques to analyse chemical data, and the process whereby the data are transformed into information used for decision making purposes [Geladi, P., 2003, Spectrochimica Acta Part B Atomic Spectroscopy 58(5):767-782]. Chemometrics enables the reduction of information contained in enormous data matrices to more easily understand information and a residual noise component. General information regarding chemometrics and chemometric analysis techniques may be found in, for example, Beebe et al. (1998) Chemometrics: a Practical Guide, NY, U.S.A.: John Wiley & Sons, Inc. For specific information regarding chemometric analysis techniques of RS data, see, e.g., Heise and Winzen (2002) Chemometrics in near-infrared spectroscopy, In: Near-Infrared Spectroscopy: Principles, Instruments, Applications, supra, pp. 125-61.

In a so called multivariate chemometric data analysis process, a chemometric analysis is applied to a data matrix in order to extract relevant information from the matrix. Analysis results may be expressed in a variety of ways, for example and without limitation, spectral data involving peak heights, absorbances, concentration, particle counts, and the like. A general term to describe these expressions is a variable. In great simplification and depending on the method applied, when variables are measured, the resulting data can be arranged in a data matrix. In brief, chemometrics involves taking the resulting data matrix and extracting hidden and meaningful information about the variables, which is made possible by correlation between many of the variables.

Chemometric analysis operates on the principle that the data matrix contains redundant information that can be reduced. The reduced terms are easier to interpret and understand, have more stability, and are separated from a residual that contains noise and/or less useful information. The reduced terms are also sometimes referred to as "latent variable". Different forms of data analysis (e.g., whether the analysis includes data exploration, classification, or curve resolution) require the utilization of different chemometric techniques. Classification of data into different groups may be performed by many different mathematical analysis methods. For example, if no information is known about the samples, the classification can be performed using unsupervised classification techniques such as principal component analysis (PCA). Alternatively, when sufficient information is available, supervised classification techniques may be more appropriate.

Advantageous approaches include for example Multiple Linear Regression (MLR), Principal Component Regression (PCR), and Partial Least Squares (PLS) regression. In further advantageous embodiments, modelling non-linear correlations can be performed using e.g. Implicit Non-linear Latent Variable Regression (INLR) or Nonlinear Iterative Partial Least Squares (NIPALS) algorithm. As it will be apparent to the technically skilled, there further exist many variations, for example NIPALS alone can be implemented in several different ways. Further, when it comes to striving for a classification, highly reliable methods include Partial Least Squares Discriminant Analysis (PLS-DA) and Soft Independent Modelling of Class Analogies (SIMCA). Naturally, many more methods exist and may be highly suitable to be used as a tool for the implementation of chemometric analysis as included in various the aspects of present disclosure.

Furthermore, as used herein the term "spectral threshold data" in the present context is to be interpreted as numerical data that define a threshold enabling to make a decision based on the evaluation of the wavelength-dependent deviations.

As used herein, the term "assessment" refers to the computational comparison of the wavelength-dependent deviations versus the threshold data, e.g. to determine whether a water pollutant is detected in a test water sample.

Similarly, as used herein the term "association" refers to performing computational comparison of the wavelength-dependent deviations versus the chemometric model, to determine if the wavelength-dependent deviations can be associated with any of the custom mater pollutant characteristics as defined in the chemometric model.

The general overview workflow of an exemplary embodiment of the processes as implemented by the self-learning quality analytical device according to the present invention is schematically presented in FIG. 1, wherein the key following action steps are as follows:

(1) A deep UV LIF-RS spectroscopic measurement is performed on a test water sample;

(2) The spectroscopic data obtained by (1) is compared to pure water reference spectral data and wavelength-dependent deviations from both spectra are calculated.

If the wavelength-dependent deviations are below a threshold value T, again a measurement is performed as outlined in (1).

If the wavelength-dependent deviations are exceeding the threshold value T, it is checked if a predefined and self-learning chemometric model (3) is able to explain the data;

if not, (4) a wet-laboratory chemical analysis is performed of the test water sample and the chemical parameter data is used as an input to improve the chemometric model. The processes are performed in an iterative way until (5) the self-learning chemometric model trained to predict the chemical parameter data purely based on the UV LIF-RS spectroscopic data is achieved and provides the user with a water quality assessment.

In a further embodiment of the present invention, a device for spectroscopic analysis comprises:

a conduit or a container for monitoring a liquid sample, preferably being an aqueous sample or water sample;

a deep ultraviolet (UV) spectroscopy system comprising a laser for irradiating the liquid sample inside the conduit or the container, the system being adapted to perform laser-induced fluorescence (LIF) and Raman spectroscopy (RS) measurements; and a computer comprising software for chemometric analysis; wherein the device is configured to:

receive spectral threshold data and a chemometric model defining custom analytes;

receive chemical parameters data obtained from a liquid sample analysed by a wet-laboratory non-spectroscopic technique;

initiate the chemometric analysis and update the chemometric model when the chemical parameters data is received;

receive predefined LIF-RS reference spectral data or perform a LIF-RS measurement on a reference sample, e.g. pure water sample to obtain reference spectral data comprising spectral information associated with the reference sample (e.g. spectral information associated with pure water);

perform a LIF-RS measurement on a test liquid sample to obtain and store test sample spectral data;

calibrate the test sample spectral data based on the reference spectral data, the calibration comprising scaling the test sample spectral data against the spectral information associated with the reference sample (e.g. the spectral information associated with pure water);

compare the calibrated test sample spectral data with the reference spectral data to quantify wavelength-dependent deviations;

process the wavelength-dependent deviations, wherein the processing comprises:

assessment of the wavelength-dependent deviations versus the spectral threshold data to determine whether an analyte is detected, and association of the wavelength-dependent deviations versus the chemometric model, if possible; and report to the user if an analyte is detected as a result of the assessment and, if the association was possible, identify the detected analyte.

Depending which characteristics are comprised in the chemometric model, the devices according to the present invention could e.g. identify the detected analytes or pollutants by their name or a key feature. For example, the devices can be configured to report that an unidentified pollutant was detected and at the same time that another pollutant identified e.g. as nitrate or a specific bacteria was identified above or below an acceptable value as specified in the chemometric model.

A further unique feature of the devices and methods according to the present invention is their cross-compatibility and intended cooperation with chemical testing facilities, possibly being parts of larger regional water testing infrastructures. Thus, in an advantageous embodiment, devices according to the present invention are provided comprising an activatable mechanical arrangement configured to collect upon activation, and optionally store, a certain volume of the test liquid sample, preferably being test aqueous sample or water sample, which volume can be easily retrieved and provided to such chemical facilitates for further analysis by a wet-laboratory non-spectroscopic technique. Such arrangements may e.g. comprise a conduit and a valve (or a series thereof) or a pump and can be configured to divert a portion of test liquid to an easily accessible container within or outside the device. The activation of the mechanical arrangement can be done by any means known in the art, usually it will involve electrical current signals triggering the action of such exemplary valve or pump.

In an advantageous embodiment, the mechanical arrangement is activated if an analyte or a pollutant/contaminant is detected, as a result of the assessment, preferably in an automatic manner when a certain condition is met. In practical terms, such condition can e.g. be an information of exceeding an acceptable value by the detected analyte, or the fact the detected analyte cannot be identified or matched to any of the characteristics of the chemometric model. The latter condition is a clear indication that a wet-laboratory analysis is needed for identifying the detected analyte, as well as for updating the chemometric model. Hence, in another preferred embodiment, devices are provided wherein the mechanical arrangement is activated if the association of a detected analyte with the chemometric model was not possible. In such instance, the volume of the test sample is collected, and the devices advantageously store the test samples' spectral data for updating the chemometric model when it receives the chemical parameters data associated with the same sample after the wet laboratory analysis of the collected test sample is completed. In a further embodiment of the present invention a volume of a test sample may be taken at periodic intervals independent from the detection of an analyte.

The collected volume of the test sample can be sent for analysis by a wet laboratory non-spectroscopic technique by many different ways. The procedure can be conducted in an entirely non-robotic way, e.g. the collected volume is removed from the device manually and then send to a chemical analyses laboratory, after which the results are returned, and a device user inputs the chemical parameters data into the device's computer. Alternatively, different degrees of automation are possible. For example, the wet chemistry lab can send an electronic file with the chemical parameters data directly to the device connected to a network, or can send the results data to an intermediate facility which will adapt the results data to an acceptable format for the device, and then send the chemical parameters data thereto.

In certain advantageous embodiments, the device can be connected to or comprise one or more non-spectroscopic chemical analysis subunits adapted to receive at least a portion of the collected volume of the test sample and analyse said volume a wet-laboratory non-spectroscopic technique. The device can in a further embodiment be adapted to receive at least a part of the chemical parameters data from said subunit, and upon this receiving, if possible and the data is complete, initiate the chemometric analysis and update the chemometric model. In such embodiment the subunit may be a robot that performs sampling and analysis with classical wet laboratory techniques and sends the thus obtained chemical parameters data to the signal processing unit of the device. Such automatic analysis robotic devices are known in the art and can perform analyses involving e.g. pH, boiling point, solubility, acidity, basicity, thermal conductivity, net charge, specific heat capacity, molar entropy, isotope fractionation, surface tension, pressure, specific resistance, compressibility, wettability, reactivity and levelling grade viscosity measurements, measurement of optical properties including odour and/or refractive index and/or taste, hyperspectral remote sensing, cytometry, measurement, total organic carbon measurements (TOC), dissolved organic carbon measurement (DOC), chemical oxygen demand measurement (COD), measurement of atmospheric conditions, conductivity measurements, volatile organic compounds measurements (VOC), mass spectrometry, gas chromatography or even high performance liquid chromatography (HPLC).

Although adding robotic non-spectroscopic chemical analysis subunits is technically feasible, they still tend to be costly. Moreover, in certain industries, certain centralised laboratory analyses performed in accordance with applicable guidelines or by a certified laboratories are often strictly required. As the devices and methods according to the present invention aim to be in compliance and collaborate with such officially existing framework, in another advantageous embodiment, devices according to the invention comprise a dispatching sub device adapted to dispatch the collected volume of the test sample. In a simplest form, such dispatching sub device can be construed as a moving platform or an ejectable storage compartment that transports the collected volume to a predefined location inside or outside of the device, from which a user or a courier service can easily access it and further dispatch it to a chemical analysis laboratory for the required analyses. In a possible embodiment, such ejectable storage compartment can be used as packaging or can be a box. The dispatching sub device can also possible be or comprise a delivery drone. In further embodiments of the present invention, the dispatching sub device can further be programmed to send a notification to a user, e.g. via a smartphone app, or automatically establish communication with a courier service.

In a preferred embodiment of the devices according to the present invention at least a part of the chemical parameters data is received from an experimental laboratory where to at least a portion of the collected volume of the test sample was dispatched.

In further embodiments, devices according to the present are provided wherein the chemometric analysis is carried out on at least the test sample spectral data, preferably as stored by the devices, versus the chemical parameters data. Naturally, in preferred embodiments the chemical parameters data is obtained from the collected volume of the test sample that was the same test sample from which the test sample spectral data was obtained.

In a further aspect of the present invention, devices are provided wherein the updating of the chemometric analysis comprises defining of a new characteristic that was undefined in the chemometric model prior to the updating. This may for example be a new analyte or specifically a water pollutant name. Alternatively, the updating may comprise changing or fine-tuning a characteristic as initially defined in the chemometric model prior to the updating, like improving concentration estimation for one of the initially defined water pollutants.

In further advantageous embodiments, the devices of the present invention are connectable to a liquid sample supply source, preferably being aqueous sample or water supply source such as, e.g. fresh or drinking water supply, various water treatment plants, water quality control in a factory or an industrial production park. Preferably, once established, the connection is executed such that the liquid sample from said source is being continuously transported in the conduit over a defined period, and preferably is being at least spectroscopically analysed in real-time, at least over the same or another defined period.

In other advantageous embodiments, the devices according to the present invention can be configured to trigger an alarm when an unknown or dangerous analyte, as defined in or missing from the chemometric model, respectively, is detected, or when an analyte is detected at an undesirable amount.

In another embodiment of the present invention, such operating in real-time devices can further be configured to communicate with said liquid supply source and, optionally, when an unknown or dangerous or undesired analyte is detected, to automatically shut off the supplying of the liquid from said liquid supply source to a downstream destination, or to diver it to another route, e.g. leading to a wastewater treatment plant. In other words, the output quality data as reported and assessed by presently disclosed devices can immediately be used to mitigate potential hazardous substance detection and control subsequent liquid processing steps. An example of this could be removing the polluted water from an industrial process and/or redirecting it for a water treatment. Another example could be removal of a contaminated batch of a diary product or other food product from production line. Such solutions would be of enormous value in many industries where high-quality processing is key, or example in production of cosmetics, as well as in food and beverage industry, notably including brewing where frequently the final products' organoleptic properties heavily depend on water quality or other properties like pH etc. Other industries include but are not limited to chemical industry, automotive and aircraft industry, steel and power generation, glass manufacture and coating, paint production, semiconductor industry, pharmaceutical industry including drug production, phytopharmaceutical industry, diagnostics, agriculture, biotechnology, wastewater industry, drinking water industry, as well as production of oils and fuels.

In further embodiments, the devices or computer-implemented methods according to the present invention may be further configured to divide at least the LIF-RS measurement data into wavelength ranges and possibly to quantify wavelength-dependent deviations at higher data granularity or resolution within a selection of said ranges. Such embodiments allow to zoom in and/or better distinguish between substances that are chemically similar and/or may have similar spectra. Such issues can occur during assessment of organic load and micropollutants, when analysing pesticides and certain groups of drugs. A further advantage of focusing only on a selection of wavelength ranges is a possible saving on computing power where other less information-rich wavelength ranges are excluded from the computations.

As used in context of computer data herein, the verb "receive" or any grammatical form thereof, such as "receiving", in addition to its conventional meaning whereby data is made available to a computer in a language that the computer understands and can process, is to also be construed as meaning that the computer data can optionally also be stored, either locally or on a cloud, having the effect that at least for some time, the received or processed data is not immediately lost after the processing.

Hence, in likely embodiments, the disclosed devices will be configured to store locally or remotely, such as on a cloud, at least any of the following: the measurement data, raw or processed, spectral threshold data, different chemometric model versions such as the initial chemometric model as well as its updated versions etc. Alternatively, the disclosed devices may send any of said data to a defined location, preferably wherein the data is encrypted. Said defined locations may include, but are not limited, another device as disclosed herein, a user's computer, a local water supply, laboratory etc. Advantageously, it can also be a facility specialised in chemometric analyses and disposing of high-computing power capabilities enabling integration of data from e.g. clusters of locally installed and on-site operating devices according to the disclosure. Such facility could have access to great amount of data from the great many of locally, regionally, or even globally operating devices of the disclosure and use it for performing high-throughput analyses leading to development of very powerful chemometric models for efficient predictions of great many substances worldwide.

In further possible embodiments, the devices according to the present invention may comprise data or result presentation functionality, which can be a screen with a graphic user interface (GUI). In addition or alternatively, the disclosed devices may be configured to visually present or otherwise communicate data or other information like warnings via a remotely installed software such as a smartphone or tablet app. The visual presentation can be adapted to continuous reporting of the quality of the liquid involved, preferably in a user-friendly and intuitive manner. For example, they can display moving measurements 'curves plotted in real time, derivatives, charts, bars etc. In a possible concrete example, the result display functionality may be configured to grade water pollutant detection output based on pre-set criteria such as using colour coding as in street signalisation (green, yellow, red).

A further aspect of the present invention relates to a computer-implemented method for spectroscopic analysis of a liquid, preferably being an aqueous liquid or water, comprising receiving a chemometric model defining custom analytes
 receiving data from a deep ultraviolet (UV) spectroscopy system adapted to perform laser-induced fluorescence (LIF) and Raman spectroscopy (RS) measurements on a liquid sample, wherein said data comprises
  first test sample spectral data obtained from a LIF-RS measurement performed on a first test liquid sample; and
  second test sample spectral data obtained from a LIF-RS measurement performed on a second test liquid sample;
 receiving a first test sample chemical parameters data obtained from a wet-laboratory non-spectroscopic analysis of a volume of the first test liquid sample;
 carrying out chemometric analysis on the first test sample spectral data versus the first test sample chemical parameters data, and updating the chemometric model;
performing calculations comprising at least the second test sample spectral data and the updated chemometric model to identify an analyte, for example a pollutant.

In an advantageous embodiment, a computer-implemented method for spectroscopic analysis of a liquid, preferably being an aqueous liquid or water, comprises:

receiving a chemometric model defining custom analytes;
 receiving data from a deep ultraviolet (UV) spectroscopy system adapted to perform laser-induced fluorescence (LIF) and Raman spectroscopy (RS) measurements on a liquid sample, wherein said data comprises:
  reference spectral data obtained from a LIF-RS measurement performed on a reference liquid sample, or predefined LIF-RS reference spectral data for a given liquid type; and
  first test sample spectral data obtained from a LIF-RS measurement performed on a first test liquid sample; and
  second test sample spectral data obtained from a LIF-RS measurement performed on a second test liquid sample;
 receiving a first test sample chemical parameters data obtained from a wet-laboratory non-spectroscopic analysis of a volume of the first test liquid sample;
 carrying out chemometric analysis on the first test sample spectral data versus the first test sample chemical parameters data, and updating the chemometric model;
 receiving spectral threshold data;
 computing the predefined LIF-RS reference spectral data or the reference spectral data and second test sample spectral data to quantify second test sample wavelength-dependent deviations
 processing of the second test sample wavelength-dependent deviations, said processing comprising
  assessment of the second test sample wavelength-dependent deviations versus the spectral threshold data to determine whether an analyte is detected in the second test water sample, and
  association of the second test sample wavelength-dependent deviations versus the updated chemometric model, if possible; and
 reporting if an analyte is detected in the second test liquid sample and, if the association was possible, identifying the detected analyte.

In a particular further preferred embodiment, the present invention relates to a computer-implemented method for spectroscopic analysis of water, comprising:

receiving a chemometric model defining custom water pollutants
 receiving data from a deep ultraviolet (UV) spectroscopy system adapted to perform laser-induced fluorescence (LIF) and Raman spectroscopy (RS) measurements on a water sample, wherein said data comprises:
  pure water reference spectral data obtained from a LIF-RS measurement performed on a pure water sample, wherein said pure water reference spectral data comprises spectral information associated with pure water (such as Raman reference water peak); and
  first test sample spectral data obtained from a LIF-RS measurement performed on a first test water sample; and
  second test sample spectral data obtained from a LIF-RS measurement performed on a second test water sample;
 receiving a first test sample chemical parameters data obtained from a wet-laboratory non-spectroscopic analysis of a volume of the first test water sample;

carrying out chemometric analysis on the first test sample spectral data versus the first test sample chemical parameters data, and updating the chemometric model;

receiving spectral threshold data;

calibrating the test sample spectral data based on the pure water reference spectral data, the calibrating comprising scaling the test sample spectral data against the spectral information associated with pure water;

comparing the calibrated test sample spectral data with the pure water reference spectral data to quantify wavelength-dependent deviations processing of the second test sample wavelength-dependent deviations, said processing comprising assessment of the second test sample wavelength-dependent deviations versus the spectral threshold data to determine whether a water pollutant is detected in the second test water sample, and association of the second test sample wavelength-dependent deviations versus the updated chemometric model, if possible; and reporting if a water pollutant is detected in the second test water sample and, if the association was possible, identifying the detected water pollutant.

In a further and preferred embodiment of the above mentioned computer-implemented methods, said method further comprises a step of receiving a second test sample chemical parameters data obtained from a wet-laboratory non-spectroscopic analysis of a volume of the second test liquid sample or test water sample, and the step of carrying out of the chemometric analysis and updating the chemometric model comprises carrying out the chemometric analysis on the first test sample spectral data and on the second test sample spectral data versus the first test sample chemical parameters data and the second test sample chemical parameters data. This is based on a preferred analysis mode according to which, in iteration N–1, the chemometric model uses all test sample spectral data (obtained from iterations 1 to N–1) and all chemical parameter data (obtained from iterations 1 to N–1), while for N=1, a pretrained chemometric model is used.

Preferably the present invention also relates to a computer-readable medium having stored thereon an updated chemometric model as obtainable by operation of the devices of the disclosure or by performing of the computer-implemented methods of the disclosure or according to any other aspect as disclosed herein. In another aspect of the present invention, a computer-readable medium is provided, having stored thereon an updated chemometric model as obtained by operation of the devices of the disclosure or by performing of the computer-implemented methods of the disclosure or according to any other aspect as disclosed herein.

In a yet a further aspect, the present invention also relates to a computer-implemented method for updating a chemometric model for spectroscopic analysis of a liquid, comprising:

receiving a chemometric model defining custom analytes;

receiving data from a deep ultraviolet (UV) spectroscopy system adapted to perform laser-induced fluorescence (LIF) and Raman spectroscopy (RS) measurements on a liquid sample, wherein said data comprises a first test sample spectral data obtained from a LIF-RS measurement performed on a first test water sample;

receiving a first test sample chemical parameters data obtained from a wet-laboratory non-spectroscopic analysis of a volume of the first test liquid sample;

carrying out chemometric analysis on the first test sample spectral data versus the first test sample chemical parameters data, and updating the chemometric model.

In a related embodiment, a computer-implemented for updating a chemometric model is provided, the method further comprising:

receiving second test sample spectral data obtained from a LIF-RS measurement performed on a second test liquid sample; and receiving a second test sample chemical parameters data obtained from a wet-laboratory non-spectroscopic analysis of a volume of the second test liquid sample;

carrying out chemometric analysis on the first test sample spectral data and the second test sample spectral data versus the first test sample chemical parameters data and the second test sample chemical parameters data, and further updating the updated chemometric model.

In further related aspect, the present disclosure also provides a computer program comprising instructions which, when the program is executed by a computer, cause the computer to carry out any of the computer-implemented methods as disclosed above.

Lastly, provided herewith are also the different uses of the disclosed devices, computer-implemented methods, programmes, and/or computer readable media, in analysis or monitoring of a liquid, preferably in chemical industry, automotive and aircraft industry, in steel and power generation, in glass manufacture and coating, in paint production, semiconductor industry, pharmaceutical industry, preferably drug production, phytopharmaceutical industry, in diagnostics, in agriculture, in biotechnology, in wastewater industry, in drinking water industry, in cosmetics production, in food production such as in dairy production or sugar mills, or in beverage production such as in brewing, as well as in production of oils and fuels. The above uses should not be construed as limiting, as other industries and processes may likely also benefit from the herein presented devices, methods, and other products. The above should be apparent from the general idea as evident from the following example showing operation of an embodiment of the presented herein device.

Figure 2:
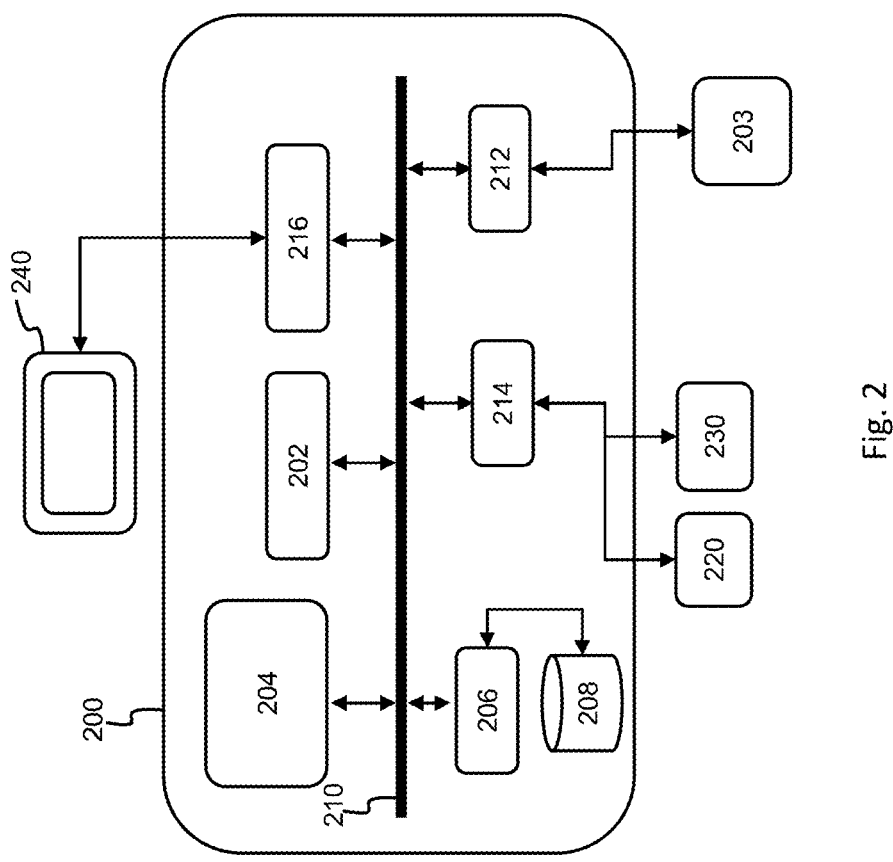
FIG. 2 shows a computer system that can be configured to execute one or more embodiments of a method for monitoring a sample of a liquid.

FIG. 2 shows a suitable computing system 200 for performing the steps according to the above embodiments. Computing system 200 may be used as a networking device for monitoring a liquid or a sample thereof. Computing system 200 may in general be formed as a suitable general purpose computer and comprise a bus 210, a processor 202, a local memory 204, one or more optional input interfaces 214, one or more optional output interfaces 216, a communication interface 822, a storage element interface 206 and one or more storage elements 208, such as a database comprising a first dataset with a first reference spectrum dataset representative for the spectral signature of a liquid, and second reference spectra datasets representative for the spectral signatures of one or more pollutants present in the liquid comprising. Bus 210 may comprise one or more conductors that permit communication among the components of the computing system 200. Processor 202 may include any type of conventional processor or microprocessor that interprets and executes programming instructions. Local memory 204 may include a random-access memory (RAM) or another type of dynamic storage device that stores information and instructions for execution by processor 202 and/or a read only memory (ROM) or another type of static storage device that stores static information and instructions for use by processor 202. Input interface 214 may comprise one or more conventional mechanisms that permit an operator to input information to the computing device 200, such as a keyboard 220, a mouse 230, a pen, voice recognition and/or biometric mechanisms, etc. Output interface 216 may comprise one or more conventional mechanisms that output information to the operator, such as a display 240, etc. Communication interface 212 may comprise any transceiver-like mechanism such as for example one or more Ethernet interfaces that enables computing system 800 to communicate with other devices and/or systems. The communication interface 212 of computing system 200 may be connected to such another computing system by means of a local area network (LAN) or a wide area network (WAN) such as for example the internet. Storage element interface 806 may comprise a storage interface such as for example a Serial Advanced Technology Attachment (SATA) interface or a Small Computer System Interface (SCSI) for connecting bus 210 to one or more storage elements 808, such as one or more local disks, for example SATA disk drives, and control the reading and writing of data to and/or from these storage elements 208. Although the storage elements 208 above is described as a local disk, in general any other suitable computer-readable media such as a removable magnetic disk, optical storage media such as a CD or DVD,—ROM disk, solid state drives, flash memory cards, . . . could be used. The system 200 described above can also run as a virtual machine above the physical hardware.

Figure 3:
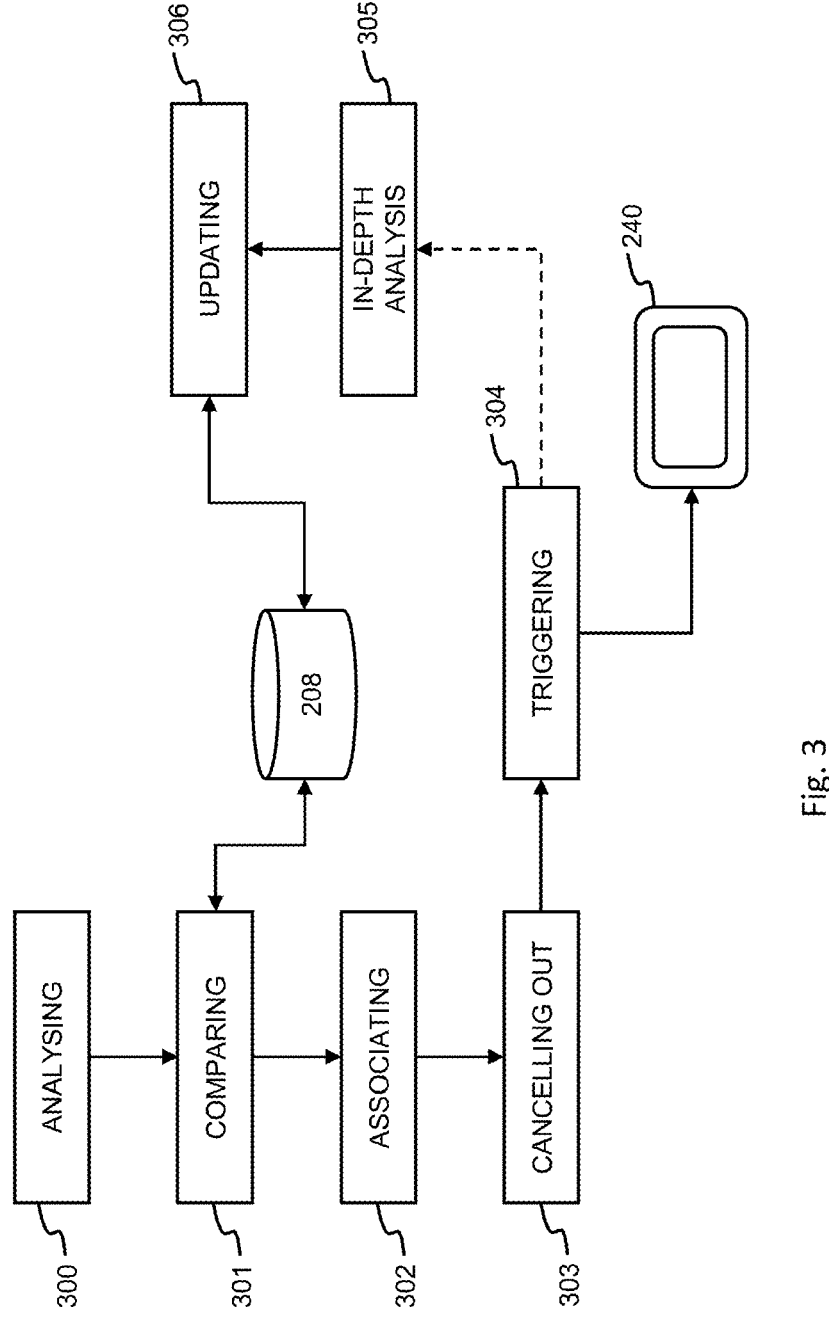
FIG. 3 illustrates steps performed to monitor a liquid or a sample thereof according to an embodiment of the invention.

In FIG. 3 steps performed by the method according to an embodiment are illustrated. In a first step 300, the liquid or a sample thereof are analysed 300 thereby generating a dataset representative for the chemical composition of the liquid. The dataset is compared 301 with the data in the database 208. Next, by the comparing step 301, one or more pollutants are associated 302, and from the dataset the first reference spectrum dataset and second reference spectra datasets of the associated 302 pollutants are cancelled out 303 thereof. If then one or more outliners are detected, an event is triggered 304 and, for example, displayed on screen 240. This gives a user an instruction to perform an in-depth analysis 305 step, whereby the data in the database 208 maybe subsequently be updated 306.

EXAMPLE

A device according to the present disclosure is used in a plant that monitors the treatment of wastewater to fresh water. The wastewater is continuously monitored by the device with LIF-RS and spectra are obtained every minute. Each spectrum is compared to the pure water reference spectral data. A pre-trained chemometric model is used to determine key water quality parameters automatically based on the obtained LIF-RS measurements spectra.

In case a novel pollutant is introduced into the wastewater, the comparison of the test water spectra with the pure water reference spectral data will cause a strong signal in the wavelength-dependent deviations of both spectra. In such event, the existing chemometric model will not be sufficient to explain the LIF-RS spectral data, triggering the automatic sampling of the water and analysing it by wet-laboratory chemical analysis.

The wet-laboratory chemical analysis is performed automatically with a device including a robotic sampling mechanism and an automatic high-performance liquid chromatography (HPLC) analysis. The HPLC data is then automatically send to a processing unit that updates the chemometric model.

This processing and analysis step is repeated until the novel chemometric model is able to correctly identify and quantify the novel pollutant only with LIF-RS without using the wet-laboratory chemical analysis. The updated model is then used for the further analysis of the water, until another novel pollutant is introduced into the wastewater.

Clauses

A device for spectroscopic analysis of a liquid, the device comprising:

a conduit or a container for monitoring a liquid sample;

a deep ultraviolet (UV) spectroscopy system comprising a laser for irradiating the liquid sample inside the conduit or the container, the system being adapted to perform laser-induced fluorescence (LIF) and Raman spectroscopy (RS) measurements, further referred to as LIF-RS measurements; and a computer comprising software for chemometric analysis;

wherein the device is configured to:

receive spectral threshold data and a chemometric model defining custom analytes;

receive chemical parameters data obtained from a liquid sample analysed by a wet-laboratory non-spectroscopic technique;

initiate the chemometric analysis and update the chemometric model when the chemical parameters data is received;

receive predefined LIF-RS reference spectral data or perform a LIF-RS measurement on a reference liquid sample to obtain reference spectral data, and perform a LIF-RS measurement on a test liquid sample to obtain test sample spectral data, then compute the reference spectral data and test sample spectral data to quantify wavelength-dependent deviations;

process the wavelength-dependent deviations, wherein the processing comprises:

assessment of the wavelength-dependent deviations versus the spectral threshold data to determine whether an analyte is detected, and association of the wavelength-dependent deviations versus the chemometric model, if possible; and report if an analyte is detected and, if the association was possible, identify the detected analyte.

The liquid sample is an aqueous sample, preferably water.

The device may further comprise an activatable mechanical arrangement configured to collect a volume of the test liquid sample, preferably wherein the mechanical arrangement is activated when an analyte is detected and/or if the association was not possible.

The device may further comprise a subunit adapted to receive and analyse the collected volume by a wet-laboratory non-spectroscopic technique, and wherein the device is further adapted to receive the chemical parameters data from said subunit.

It may further comprise a dispatching sub device adapted to dispatch the collected volume, the dispatching sub device preferably being selected from an ejection platform, a delivery drone, or a boxing machine, possibly programmed to send a notification to a user or establish communication with a courier service.

The chemical parameters data may be received from an experimental laboratory where to the collected volume was dispatched.

The chemometric analysis may be carried out on at least the test liquid sample spectral data versus the chemical parameters data.

The device may be connectable to a liquid sample supply source, such that the liquid sample from said source is being transported in the conduit over a defined period, and preferably is being at least spectroscopically analysed in real-time.

It may further be configured to communicate with said liquid sample supply source and automatically shut off the liquid sample supplying from said source to a downstream destination, preferably when an unknown or dangerous analyte is detected or when an analyte is detected at an undesirable amount.

Finally, it may further be configured to divide at least the LIF-RS measurement data into wavelength ranges and possibly to quantify wavelength-dependent deviations at higher data granularity or resolution within a selection of said ranges.

Further, a computer-implemented method is disclosed for spectroscopic analysis of a liquid, comprising:

receiving a chemometric model defining custom analytes
receiving data from a deep ultraviolet (UV) spectroscopy system adapted to perform laser-induced fluorescence (LIF) and Raman spectroscopy (RS) measurements on a liquid sample, wherein said data comprises
  first test sample spectral data obtained from a LIF-RS measurement performed on a first test liquid sample; and
  second test sample spectral data obtained from a LIF-RS measurement performed on a second test liquid sample;
receiving a first liquid test sample chemical parameters data obtained from a wet-laboratory non-spectroscopic analysis of a volume of the first test liquid sample;
carrying out chemometric analysis on the first test sample spectral data versus the first test sample chemical parameters data, and updating the chemometric model;
performing calculations comprising at least the second test sample spectral data and the updated chemometric model to identify an analyte.

A second computer-implemented method for spectroscopic analysis of a liquid is disclosed, comprising:

receiving a chemometric model defining custom analytes;
receiving data from a deep ultraviolet (UV) spectroscopy system adapted to perform laser-induced fluorescence (LIF) and Raman spectroscopy (RS) measurements on a liquid sample, wherein said data comprises:
  reference spectral data obtained from a LIF-RS measurement performed on a reference liquid sample, or predefined LIF-RS reference spectral data for a given liquid type; and
  first test sample spectral data obtained from a LIF-RS measurement performed on a first test liquid sample; and
  second test sample spectral data obtained from a LIF-RS measurement performed on a second test liquid sample;
receiving a first test sample chemical parameters data obtained from a wet-laboratory non-spectroscopic analysis of a volume of the first test liquid sample;
carrying out chemometric analysis on the first test sample spectral data versus the first test sample chemical parameters data, and updating the chemometric model;
receiving spectral threshold data;
computing the reference spectral data and second test sample spectral data to quantify second test sample wavelength-dependent deviations
processing of the second test sample wavelength-dependent deviations, said processing comprising
  assessment of the second test sample wavelength-dependent deviations versus the spectral threshold data to determine whether an analyte is detected in the second test sample, and
  association of the second test sample wavelength-dependent deviations versus the updated chemometric model, if possible; and
reporting if an analyte is detected in the second test liquid sample and, if the association was possible, identifying the detected analyte,
preferably wherein the computer-implemented method further comprises receiving a second test sample chemical parameters data obtained from a wet-laboratory non-spectroscopic analysis of a volume of the second test liquid sample, and
wherein the step of carrying out of the chemometric analysis and updating the chemometric model comprises carrying out the chemometric analysis on the first test sample spectral data and on the second test sample spectral data versus the first test sample chemical parameters data and the second test sample chemical parameters data.

A third computer-implemented method for updating a chemometric model for a spectroscopic analysis of a liquid is disclosed, the method comprising receiving a chemometric model defining custom analytes
receiving data from a deep ultraviolet (UV) spectroscopy system adapted to perform laser-induced fluorescence (LIF) and Raman spectroscopy (RS) measurements on a liquid sample, wherein said data comprises a first test sample spectral data obtained from a LIF-RS measurement performed on a first test sample;
receiving a first test sample chemical parameters data obtained from a wet-laboratory non-spectroscopic analysis of a volume of the first test liquid sample;
carrying out chemometric analysis on the first test sample spectral data versus the first test sample chemical parameters data, and updating the chemometric model,
preferably wherein the computer-implemented method further comprises:
receiving second test sample spectral data obtained from a LIF-RS measurement performed on a second test liquid sample; then
receiving a second test sample chemical parameters data obtained from a wet-laboratory non-spectroscopic analysis of a volume of the second test liquid sample; and
carrying out chemometric analysis on the first test sample spectral data and the second test sample spectral data versus the first test sample chemical parameters data and the second test sample chemical parameters data, and further updating the updated chemometric model.

A computer program is disclosed comprising instructions which, when the program is executed by a computer, cause the computer to carry out the first, second and/or third method as discussed above.

A computer-readable medium is disclosed having stored thereon the updated chemometric model as obtained by operation of the device as discussed above or by performing of the first, second, and/or third computer-implemented method.

Use of the device as discussed above, or the first, second, and/or third computer-implemented method as discussed above, or the computer program according as discussed above, or the computer readable medium as discussed above for analysis or monitoring of a liquid, preferably in chemical industry, automotive and aircraft industry, in steel and power generation, in glass manufacture and coating, in paint production, semiconductor industry, pharmaceutical industry, preferably drug production, phytopharmaceutical industry, for medical diagnostics, in agriculture, in biotechnology, in wastewater industry, in drinking water industry, in cosmetics production, in food production such as in dairy production or sugar mills, or in beverage production such as in brewing, as well as in production of oils and fuels is disclosed.

The invention claimed is:

1. A computer-implemented method for monitoring a sample of a liquid, the method comprising the steps of iteratively performing:

analysing the sample by a combined laser-induced fluorescence (LIF) and Raman spectroscopy (RS) measurement thereby obtaining a first dataset representative for the spectral signature of the sample;

comparing the first dataset with a first reference spectrum dataset representative for the spectral signature of the liquid thereby obtaining a spectral deviation dataset;

associating the spectral deviation dataset with second reference spectra datasets representative for spectral signatures of one or more pollutants present in the liquid;

cancelling out the first dataset with the first reference spectrum dataset and second reference spectra datasets of associated pollutants thereby obtaining a spectral threshold dataset; and when one or more values of the spectral threshold dataset exceeds a predefined value, triggering an event for indicating the one or more values as outliners.

2. The computer-implemented method according to claim 1, wherein the second reference spectra datasets are further representative for respective concentrations of the one or more pollutants present in the liquid.

3. The computer-implemented method according to claim 1, further comprising the step of:

reporting the one or more pollutants when associated.

4. The computer-implemented method according to claim 1, wherein when the event is triggered, the method further comprises the step of:

updating the second reference spectra datasets based on data received from an analysis step for identifying the outliners as one or more additional pollutants.

5. The computer-implemented method according to claim 1, wherein the method further comprises the step of:

reporting a health status of the liquid based on the spectral threshold dataset and/or the event.

6. The computer-implemented method according to claim 1, wherein the event comprises one or more of:

an alarm;

a sound;

sending and/or projecting a report, email, and/or text message; and a light.

7. The computer-implemented method according to claim 1, further comprises the step of:

instructing an interrupting means of a process arranged to use the liquid to interrupt the process.

8. The computer-implemented method according to claim 1, wherein the analysing further comprises measuring from the sample a parameter of one or more of the group of a pH value, a temperature, a turbidity, and/or a conductivity; and wherein the first dataset, the first reference spectrum dataset, and the second reference spectra datasets are normalized dataset based the parameter; and wherein the steps are performed by taking into account the parameter.

9. The computer-implemented method according to claim 1, wherein the liquid is water.

10. A system for spectroscopic analysis of a liquid, the system comprising:

monitoring means for monitoring the liquid in a conduit and/or a container via a deep ultraviolet (UV) spectroscopy arrangement comprising a laser for irradiating the liquid, the arrangement being adapted to perform laser-induced fluorescence (LIF) and Raman spectroscopy (RS) measurements; and a processing unit configured to receive data from the UV spectroscopy arrangement and to perform the method according to claim 1 based on the received data.

11. A device for spectroscopic analysis of a liquid, the device comprising:

a conduit and/or a container;

a deep ultraviolet (UV) spectroscopy arrangement comprising a laser for irradiating the liquid, the arrangement being adapted to perform laser-induced fluorescence (LIF) and Raman spectroscopy (RS) measurements of the liquid in the conduit and/or container; and a processing unit configured to receive data from the UV spectroscopy arrangement and to perform the method according to claim 1 based on the received data.

12. The device according to claim 11, further comprising displaying means for presenting information indicative for the associated one or more pollutants and/or the event.

13. The device according to claim 11, further comprising a mechanical arrangement configured to collect a volume of the liquid, wherein the mechanical arrangement is activatable based on the associated one or more pollutants and/or the event.

14. The device according to claim 13, wherein the mechanical arrangement is detachable.

15. The device according to claim 11, wherein the conduit and/or container are configured to be connectable to a supply source of the liquid.

16. The device according to claim 15, further comprising blocking means configured to block the supply source based on associated one or more pollutants and/or the event.

17. A non-transitory computer readable medium having stored thereon a computer program product comprising instructions that, when executed, causes a computer to execute the steps of the method of claim 1.

18. A database comprising means for interacting with a data processing apparatus system comprising means for carrying out the method of claim 1, the database having stored thereon a first dataset with a first reference spectrum dataset representative for the spectral signature of a liquid, and second reference spectra datasets representative for the spectral signatures of one or more pollutants present in the liquid.

\* \* \* \* \*